(12) United States Patent
Langlois et al.

(10) Patent No.: US 8,535,721 B2
(45) Date of Patent: Sep. 17, 2013

(54) PHARMACEUTICAL MICROSPHERES CONTAINING VALPROIC ACID FOR ORAL ADMINISTRATION

(75) Inventors: Christian Langlois, Verrieres le Buisson (FR); Jean-Yves Lanne, Bordeaux (FR)

(73) Assignee: Sanofi-Synthelabo, Paris (FR)

( * ) Notice: Subject to any disclaimer, the term of this patent is extended or adjusted under 35 U.S.C. 154(b) by 1493 days.

(21) Appl. No.: 11/357,426

(22) Filed: Feb. 21, 2006

(65) Prior Publication Data

US 2006/0263437 A1 Nov. 23, 2006

Related U.S. Application Data

(63) Continuation of application No. 10/270,159, filed on Oct. 15, 2002, now abandoned, which is a continuation of application No. 09/147,788, filed as application No. PCT/FR97/01762 on Oct. 3, 1997, now abandoned.

(30) Foreign Application Priority Data

Oct. 7, 1996 (FR) ...................................... 96 12201

(51) Int. Cl.
*A61K 9/14* (2006.01)
(52) U.S. Cl.
USPC ....................................................... 424/489
(58) Field of Classification Search
None
See application file for complete search history.

(56) References Cited

U.S. PATENT DOCUMENTS

| | | | | |
|---|---|---|---|---|
| 4,913,906 A | * | 4/1990 | Friedman et al. | 424/499 |
| 5,017,613 A | * | 5/1991 | Aubert et al. | 514/557 |
| 5,185,159 A | * | 2/1993 | Aubert et al. | 424/489 |
| 5,283,065 A | * | 2/1994 | Doyon et al. | 424/467 |
| 5,320,853 A | * | 6/1994 | Noda et al. | 424/472 |
| 5,399,357 A | * | 3/1995 | Akiyama et al. | 424/457 |
| 5,690,959 A | * | 11/1997 | Palepu et al. | 424/472 |

OTHER PUBLICATIONS

Giannola et al. "Preparation of White Beeswax Microspheres Loaded with Valproic Acid and Kinetic Study of Drug Release", Drug Development and Industrial Pharmacy, vol. 21, No. 7, pp. 793-807, 1995.*
Giannola et al.,"Preparation of White Beeswax Microspheres Loaded with Valproic Acid and Kinetic Study of Drug Release," *Drug Development and Industrial Pharmacy*, vol. 21, No. 7, pp. 793-807, 1995.
Giannola et al., "In vitro evaluation of cumulative release of valproic acid and vitamin E from hexadecanol microspheres," *Pharmazie*, vol. 48, No. 12, 1993; pp. 917-920.
Giannola et al., "Carnauba Wax Microspheres Loaded with Valproic Acid: Preparation and Evaluation of Drug Release," *Drug Development and Industrial Pharmacy*, vol. 21, No. 13, pp. 1563-1572, 1995.

* cited by examiner

*Primary Examiner* — Susan Tran
(74) *Attorney, Agent, or Firm* — Finnegan, Henderson, Farabow, Garrett & Dunner LLP

(57) ABSTRACT

The subject of the invention is pharmaceutical microspheres containing, as active principle, a mixture of valproic acid and of one of its pharmaceutically acceptable salts in combination with a matrix vehicle selected from glycerol esters, hydrogenated oils, esterified polyethylene glycols, waxes and their mixtures.

28 Claims, 2 Drawing Sheets

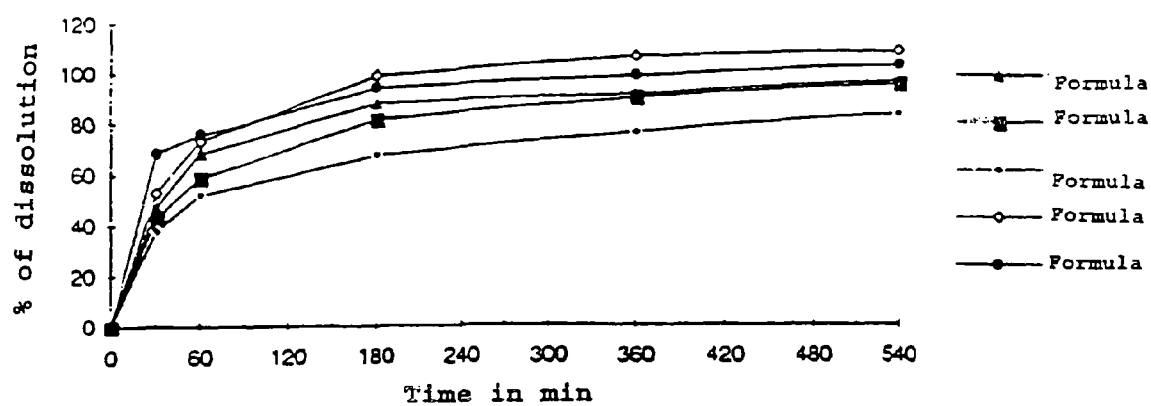
FIG. I
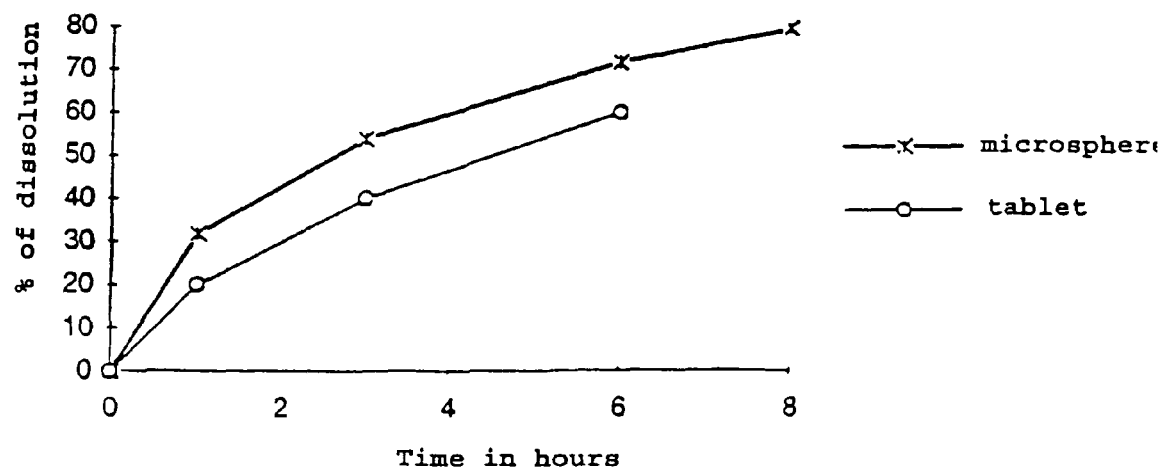
FIG. II

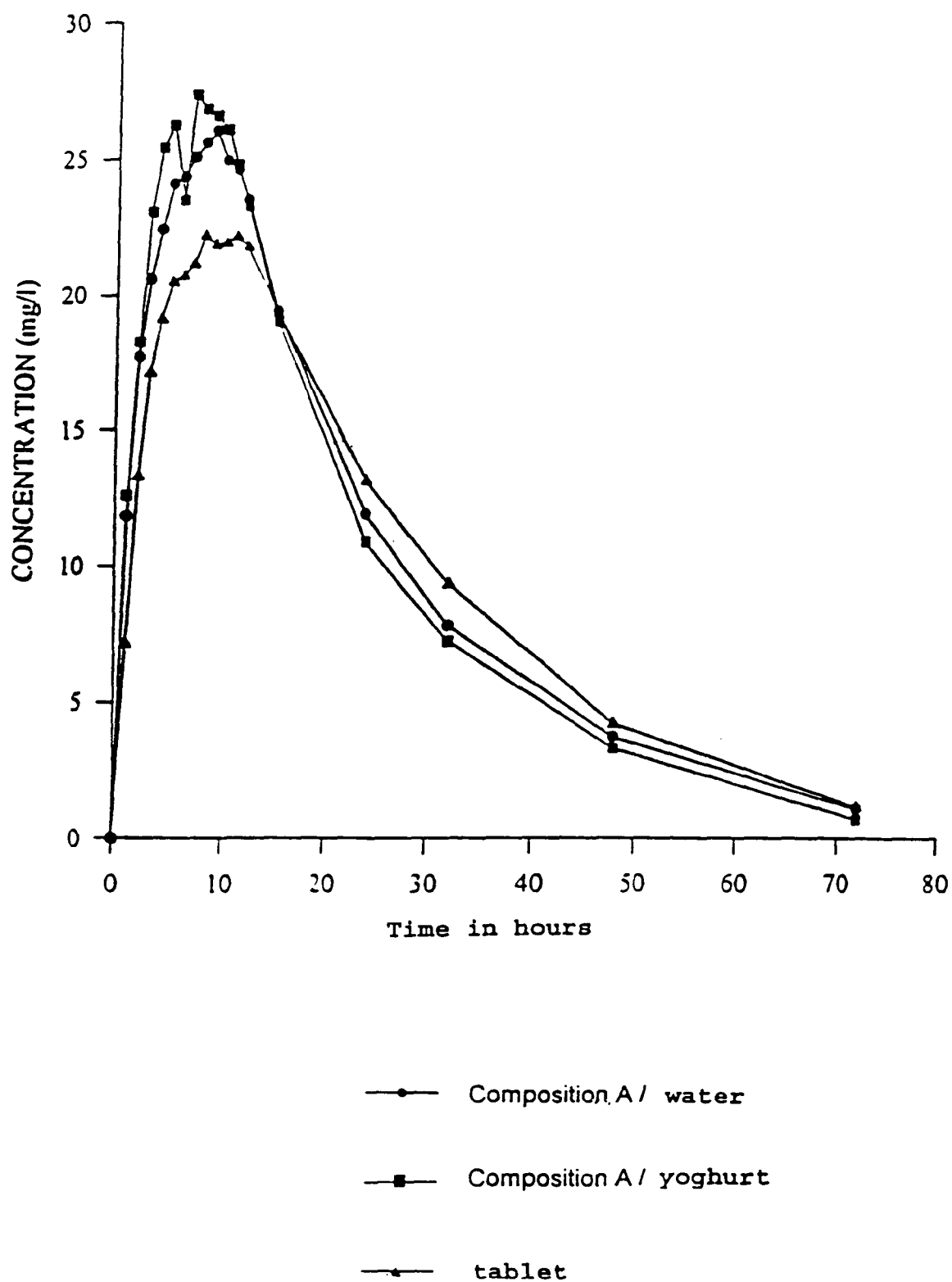
FIG. III

PHARMACEUTICAL MICROSPHERES CONTAINING VALPROIC ACID FOR ORAL ADMINISTRATION

CROSS-REFERENCE TO RELATED APPLICATIONS

This is a continuation of Ser. No. 10/270,159, filed Oct. 15, 2002 now abandoned, which is a continuation of application Ser. No. 09/147,788 filed Jul. 23, 1999 now abandoned, which is a 371 of PCT/FR97/01762, filed Oct. 3, 1997.

This application is based on and claims the benefit of U.S. application Ser. No. 09/147,788, filed Jul. 23, 1999, (now abandoned), which is a §371 Application of PCT/FR97/01762, filed Oct. 3, 1997. The entire disclosure of these applications are relied upon and incorporated by reference herein.

FIELD OF THE INVENTION

The present invention generally relates to new pharmaceutical microspheres for oral administration.

In particular, the invention relates to new pharmaceutical microspheres for oral administration containing valproic acid of formula:

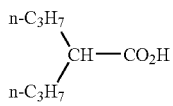

and one of its pharmaceutically acceptable salts, in particular an alkali metal, such as sodium or potassium, or alkaline-earth metal, such as calcium or magnesium, salt.

BACKGROUND OF THE INVENTION

Sodium valproate is an anti-epileptic medicament widely sold at the current time, in particular in the form of tablets assaying 500 mg per administration unit.

These tablets, which are provided with an enteric or programmed-release coating, are for this reason fairly large.

In consequence, such tablets will generally be disadvantageous, in particular for children or people experiencing difficulties in swallowing, for example elderly people.

For this type of patient, it thus appears desirable to have available administration forms which are better suited to their state or to their condition.

Moreover, sodium valproate has a rather unpleasant, bitter taste. It will consequently prove to be necessary to take into account this disadvantage in administration forms suitable for children, for example syrup forms or solutions to be taken orally, by masking this taste using various expedients.

However, administration forms such as syrups do not allow children to benefit from the advantages resulting in some cases from the gastroresistance and the prolonged release of the active ingredient.

Moreover, the adjustment of the dose of active ingredient to the weight of the child, the child posology per kg of body weight being observed, represents an additional constraint in paediatrics.

A few years ago, a new pharmaceutical dosage presentation appeared which makes it possible to satisfy some of these requirements. It consists of a fine semolina composed of microspheres, in which microspheres the active ingredient is most often covered with an isolating film. This fine semolina, sprinkled over a spoonful of semi-solid food, for example purée, compote or yoghurt, is administered as is.

However, the so-called microsphere pharmaceutical form lends itself poorly to sustained release of the active ingredient. This is because, for equal masses, the surface area developed by these spheres will increase as their diameter becomes smaller, the consequence of which will be that these microspheres dissolve faster.

In order to overcome this disadvantage, it will generally be recommended to provide these spheres with an appropriate coating which makes possible the desired delayed release.

While it is industrially possible to coat pharmaceutical microspheres, it is however lengthy because it requires a large amount of polymer to be deposited.

Various methods for manufacturing these microspheres, sometimes known as "prills", are known and have been experimented with for various active ingredients.

One of them, applied to valproic acid, has been described in "Drug Development and Industrial Pharmacy", 21(7), pp. 793-807 (1995).

According to this process, a mixture composed of white beeswax in the molten form, valproic acid and a surface-active agent is stirred in an aqueous medium at pH=4.5 while maintaining the mixture at a temperature greater than the melting temperature of the wax. On cooling, the spherical particles formed by dispersion solidify as microspheres.

However, the mean concentration of valproic acid in these microspheres does not exceed 17%, these microspheres having a certain concentration of the surfactant used, namely a mixture of ethoxylated or non-ethoxylated polysorbates.

Another technique for forming pharmaceutical microspheres resorts to the prilling technique.

According to this technique, described in particular in Pat. DE 2,725,924, an excipient, the melting point of which is less than 120° C., is melted, the dissolved or dispersed active ingredient can be added thereto and then this molten dispersion is passed through a vibrating nozzle which causes the jet to break up and spherical droplets to form, which cool as microspheres in falling.

This process has been applied, for example, to pharmaceutical ingredients with an undefined crystallization point which melt in the excipient, as described in patent EP 438, 350. This excipient can be, for example, a fatty alcohol, such as stearyl alcohol, a fatty acid, such as stearic acid, a glycerol ester, a hydrogenated oil, a fatty acid salt, a polyol, a wax, a polyoxyethylene glycol or an esterified polyoxyethylene. Moreover, stearic acid is exemplified therein as excipient.

However, it was specified therein that, in the specific case of ketoprofen, fatty acids and their salts, glycerol esters, hydrogenated oils, waxes or esterified polyoxyethylenes alone can be used.

Other pharmaceutical ingredients have also been experimented with in the prilling technique.

Thus, tests on the manufacture of microspheres containing theophylline as active ingredient have been reported in the "Technical Bulletin", No. 83, pp 3347 (1990) of the company Gattefossé, use being made, as matrix excipient, of combinations such as stearic acid/white wax or carnauba wax/glyceryl stearate (Precirol® WL 2155), optionally with addition of saturated polyglycolysed glyceride (Gelucire® 50-13), while taking into account the characteristics of these excipients with the process chosen.

However, problems of homogeneity were recorded which resulted, according to this publication, in so-called wax mixtures being abandoned for the formation of theophylline microspheres.

In the context of the present invention, attempts were made to apply this technique to sodium valproate. However, the first tests carried out, starting with a matrix comprising a stearic derivative, demonstrated a number of problems, including crystallization of the sodium valproate in the mixture subjected to prilling and a viscosity unsuitable for the manufacture of microspheres.

These disadvantages were displayed in particular during the use of a 68/2/30 by weight mixture of stearyl alcohol/ Gelucire® 50-13/sodium valproate.

Moreover, tests making use of sodium valproate and stearic acid as excipient showed a high degree of incompatibility, since precipitation brought about by contact of these ingredients is recorded.

It consequently appears illusory to transpose to sodium valproate the matrix excipients commonly used in the prior art for the preparation of pharmaceutical microspheres by the prilling technique.

In addition, the fruitless tests reported, on the one hand, in the state of the art and, on the other hand, in the context of the present invention convincingly show that there does not exist a standard excipient which can be employed in a prilling process whatever the active pharmaceutical ingredient used.

Consequently, the development of an administration form for sodium valproate which is simultaneously easy to use in paediatrics and geriatrics, capable of masking the unpleasant taste of this active ingredient and preferentially possesses a sustained-release profile remains of undeniable interest.

SUMMARY OF THE INVENTION

It has now been found, surprisingly, that it is possible to avoid the disadvantages reported above by using, as administration form, microspheres containing, as active ingredient, sodium valproate or any other pharmaceutically acceptable salt of valproic acid and valproic acid itself, in combination with a suitably chosen matrix vehicle.

In the majority of cases, these microspheres have additionally turned out to be suitable for sustained release of the active ingredient, without requiring them to be provided with a specific coating for this purpose.

Thus, a first subject of the invention relates to pharmaceutical microspheres containing, as active principle, a mixture of valproic acid and of one of its pharmaceutically acceptable salts, such as the sodium salt, in combination with a matrix vehicle selected from glycerol esters, hydrogenated oils, esterified polyethylene glycols, waxes and their mixtures.

Another subject of the invention relates to a process for the preparation of microspheres containing a mixture of valproic acid and of a pharmaceutically acceptable salt of this acid, in combination with a matrix vehicle.

Finally, the invention relates to a pharmaceutical form for oral administration containing microspheres according to the invention.

BRIEF DESCRIPTION OF THE DRAWINGS

Figure I. Microspheres of differing formulations were subjected to dissolution tests according to the method disclosed in European Pharmaocpoeia II described below. The dissolution profiles are reproduced in FIG. 1.

Figure II. The dissolution profiles for a microsphere formulation and a tablet formulation are depicted.

Figure III. The mean blood concentration (mg/l) of valproate anion is depicted for healthy subjects treated with micropspheres of Composition A in water, microspheres of Composition A in yoghurt, and a divisible retard tablets.

DETAILED DESCRIPTION OF THE INVENTION

In the present context, both in the description and in the claims, "active principle" will denote the mixture of valproic acid and of pharmaceutically acceptable salt of this acid used in the context of the present invention.

The microspheres of the invention can be obtained according to the prilling process mentioned above, which consists:

in adding valproic acid and the pharmaceutically acceptable salt of this acid to the matrix vehicle in the molten form, so as to dissolve these active ingredients in the matrix, and maintaining the resulting mixture with stirring until a clear fluid is obtained, in forcing the mixture in the clear form thus obtained through a nozzle which is subjected to vibration, whereby droplets are formed at the outlet of the nozzle and are carried by gravity into a tower in which a cold gas, generally refrigerated air, moves in a counter-currentwise direction, in collecting the microspheres in the bottom of the tower.

If necessary, a fluidized bed can be added to this prilling tower, which bed makes it possible to keep the not yet completely solidified microspheres constantly fluidized.

In practice, the mixture used in the prilling can be obtained by heating the matrix vehicle to its melting temperature, then, when the mass is completely molten, by adding valproic acid and then a pharmaceutically acceptable salt of this acid, and by maintaining the combined mixture with stirring until a clear fluid is obtained.

Alternatively, it is also possible to prepare this mixture by adding, separately, the pharmaceutically acceptable salt of valproic acid to valproic acid itself and by then introducing the combined mixture into the molten matrix vehicle.

The microspheres of the invention contain, as active principle, a mixture in all proportions of valproic acid and of one of its pharmaceutically acceptable salts.

This salt is generally an alkali metal salt, preferably the sodium salt, or an alkaline-earth metal salt, such as the calcium or magnesium salt.

Preferentially, but not exclusively, use is made as active principle of mixtures containing at least 5% by weight either of valproic acid or of one of its pharmaceutically acceptable salts, the surplus being composed of at most 95% by weight of a pharmaceutically acceptable salt of valproic acid or of valproic acid respectively.

In particular, the active principle is composed of mixtures of 15% to 60% by weight of valproic acid and of 40% to 85% by weight of pharmaceutically acceptable salt of this acid.

Mixtures containing from 25% to 35% by weight of valproic acid and from 65% to 75% by weight of the salt in question represent mixtures which are particularly preferred for the purposes of the invention.

As a general rule, the viscosity of the composition formed by the pharmaceutical ingredient and the matrix excipient is a limiting factor in making use of the prilling process suited to the preparation of pharmaceutical microspheres.

In the present case and for this reason, the microspheres of the invention will contain at most 35% by weight of active principle, as described above, preferably from 30% to 35% by weight.

Indeed, it has been noticed that a concentration by weight of active principle greater than 35% would require a higher temperature of the matrix mass in order to maintain a sufficient viscosity of the latter for the purpose of preparing the microspheres. Moreover, a concentration of active principle greater than 35% causes difficulties of dissolution of the latter in the matrix vehicle.

This matrix vehicle, which is composed of one or of several excipients of the class of glycerol esters, hydrogenated oils, esterified polyethylene glycols, or waxes, is selected such that its melting point is between 50° C. and 120° C., generally between 70° C. and 90° C.

This matrix vehicle does not contain any additional contribution of surface-active agents, such as those of the ethoxylated or non-ethoxylated polysorbate type.

Excipients capable of melting at a temperature of the order of 80° C., the latter corresponding to the temperature which allows the active principle to be dissolved in the matrix vehicle and to the maximum temperature which can be used for good preservation of the microspheres formed, are preferably selected. Moreover, an excessively high temperature would require an excessively high drop height for the microspheres in order to achieve complete solidification, with the risk of causing the active principle to degrade.

On taking into consideration this recommended melting temperature range, the excipients in question can be selected from:

saturated or unsaturated fatty acid glycerides, in particular glycerides containing up to 80 carbon atoms, such as, for example, glyceryl tribehenate, glyceryl palmitate/stearate, glyceryl mono-stearate, glyceryl monooleate or caprylic/capric glycerides, such as glyceryl tricaprylate/caprate saturated polyglycolysed glycerides, such as mixtures of glycerol monoesters, diesters and triesters and of polyethylene glycol mono- and diesters hydrogenated oils, such as hydrogenated castor oil a wax, such as natural beeswax or synthetic beeswax or a paraffin.

By way of example, matrix excipients capable of forming microspheres according to the invention can be selected from:

glyceryl tribehenate, such as sold under the trademark Compritol® 888 glyceryl palmitate/stearate, such as sold under the trademark Precirol® AT05 a hydrogenated castor oil, such as sold under the trademark Cutina® HR glyceryl monostearate, such as sold under the trademark Monomuls® 90/25 glyceryl monooleate, such as sold under the trademark Myverol® 18/99 glyceryl tricaprylate/caprate, such as sold under the trademark Labrafac® lipophile saturated polyglycolysed glycerides, such as sold under the trademarks Gelucire® 50-02 or Labrafil® 2130CS a natural beeswax or a synthetic beeswax, such as sold under the trademark Cutina® BW a paraffin.

The excipients used in the context of the invention will furthermore be selected while taking into account the hydrophilic, lipophilic (or hydrophobic) or amphiphilic nature which they may possess and according to the kinetics desired for the release of the active principle.

In particular, and in a non-limiting way, mixtures of excipients of the type:

either glyceryl tribehenate (Compritol® 888)/surfactant (Labrafil® 2130CS)

or glyceryl tribehenate (Compritol® 888)/glyceryl monooleate (Myverol® 18/99)

or synthetic beeswax (Cutina® BW)/hydrogenated castor oil (Cutina® HR)/glyceryl monostearate (Monomuls® 90/25)

have proved to be suitable for fairly immediate release of the active principle.

By way of example, in vitro dissolution tests were carried out at pH=6.8 for 6 hours according to the method described in the monograph "Dissolution tests for solid oral forms" of the European Pharmacopoeia II in the part General Directions V. 5.4, pp. 1-9 (1995).

Microspheres comprising from 55% to 60% by weight of product Compritol® 888 or of product Precirol® ATO5, from 30% to 35% by weight of active principle (valproic acid/sodium valproate) and from 10% to 15% by weight of surfactant Labrafil® 2130CS were used for this purpose.

After 1 hour, 100% of dissolved active principle was recorded in the case of the formulation including the product Precirol® ATO5 and 85% was recorded for that comprising the product Compritol® 888.

Likewise, dissolution tests carried out under the same conditions with microspheres containing from 20% to 25% by weight of product Cutina® HR, 20% to 25% by weight of product Cutina® BW, 20% to 25% by weight of product Monumuls® 90/25 and 30% to 35% by weight of active principle (valproic acid/sodium valproate) showed 100% dissolution of the active principle after 1 hour.

Moreover, an analogous test carried out with 55% to 60% by weight of product Compritol® 888, 30% to 35% by weight of active principle (valproic acid/sodium valproate) and 10% by weight of product Myverol® 18/99 also revealed an immediate release profile.

Following these tests, it could be concluded that none of the formulations tested and exemplified above exhibits a profile of delayed release of the active principle over a period of 6 hours.

In contrast, other microsphere formulations involving the product Compritol® 888 as sole matrix excipient have proved to be fairly suitable for delayed release of the active principle.

The addition of certain hydrophobic substances, such as hydrogenated castor oil (Cutina® HR), beeswax, paraffin, the product Gelucire® 50-02 or the product Labrafac® lipophile, has furthermore made it possible to accentuate the delayed release of the active principle.

By way of example, microspheres containing from 65 to 70% by weight of the product Compritol® 888 and from 30% to 35% by weight of active principle (valproic acid/sodium valproate) have revealed, during dissolution tests, a slow dissolution profile. Analogous results were recorded from microspheres comprising from 55% to 60% by weight of the product Compritol® 888, 10% to 15% by weight of the product Cutina® HR, beeswax, paraffin, the product Gelucire® 50-02 or the product Labrafac® lipophile and 30% to 35% by weight of active principle.

In particular, microspheres with the following formulations were subjected to dissolution tests at pH=6.8 for 9 hours according to the method of the European Pharmacopoeia II described above, namely:

|  | % by weight |
|---|---|
| Compritol ® 888 | 58.37 |
| Adjuvants | 10 |
| Valproic acid | 9.63 |
| Sodium valproate | 22 |
|  | 100.00 | the adjuvants corresponding to the products Cutina® HR, Cutina® BW, paraffin, Gelucire® 50-02 and Labrafac® lipophile.

The dissolution profiles obtained are reproduced in the appended Figure I, in which figure:
a) the curve denoted "formula 1" represents the percentages of dissolution of the valproate anion as a function of the time from the above microspheres, in which microspheres the adjuvant is the product Cutina® HR
b) the curve denoted "formula 2" represents analogous percentages to the curve "formula 1", the adjuvant being the product Cutina® BW
c) the curve denoted "formula 3" represents analogous percentages to the curve "formula 1", the adjuvant being paraffin
d) the curve denoted "formula 4" represents analogous percentages to the curve "formula 1", the adjuvant being the product Gelucire® 50-02
e) the curve denoted "formula 5" represents analogous percentages to the curve "formula 1", the adjuvant being the product Labrafac® lipophile.

The results obtained show delayed-release kinetics for the active principle. It can be deduced therefrom that the formulations containing paraffin, hydrogenated castor oil (Cutina® HR) and synthetic beeswax (Cutina® BW) appear as the most advantageous.

As the active principle used in the present invention is composed of a hydrophobic component, namely valproic acid, and of a hydrophilic component, that is to say a pharmaceutically acceptable salt of this acid, it seems that the most suitable matrix excipients should be amphiphilic substances, in order, by their hydrophobic part, to provide for the delayed release of the active principle and, by their hydrophilic part, to provide for the regulation of the rate of release of this active principle from the excipient.

It has been found, unexpectedly, that a matrix excipient formed solely of natural beeswax, a typically hydrophobic fatty substance, makes possible a release profile of the active principle which is entirely compatible with a retard pharmaceutical formulation. In addition, this profile proved to be fairly similar to the release profile recorded with known tablets containing a valproic acid/sodium valproate mixture as active ingredient.

In particular, dissolution tests and pharmacokinetic tests were carried out from:
either microspheres formed of 68.37 g of natural beeswax as matrix vehicle and of 31.63 g of active principle, namely 9.63 g of valproic acid and 22 g of sodium valproate, hereinafter denoted "Composition A microspheres". The active principle consequently corresponds to a 30.45%/69.55% by weight valproic acid/sodium valproate mixture.
or a divisible retard tablet formulated with 478 mg of a valproic acid/sodium valproate mixture, namely 145 mg of acid and 333 mg of salt, this tablet comprising in particular methacrylic acid polymers as excipient.

The active ingredients of this commercial tablet consequently correspond to a 30.33%/69.67% by weight valproic acid/sodium valproate mixture or to 500 mg of active ingredient expressed as sodium valproate.

I.—Dissolution Tests

These tests were carried out in vitro at pH=6.8 according to the method cited above.

The dissolution profiles obtained are reproduced in the appended Figure II, in which figure:
a) the curve denoted "microspheres" represents the percentages of dissolution of the valproate anion as a function of the time from the above Composition A microspheres
b) the curve denoted "tablet" represents the percentages of dissolution of the valproate anion as a function of the time from the above divisible retard tablet.

The results obtained clearly show that the dissolution profile of the Composition A microspheres is close to and resembles the dissolution profile of the tablet, since a difference of only 10% separates them after the first hour, a difference which remains constant for at least 5 hours.

II.—Pharmacokinetic Tests

Tests were carried out on three series of 24 healthy subjects, to whom were administered:
Composition A microspheres in water
Composition A microspheres in yoghurt
a divisible retard tablet such as above so that each subject receives a dose of active ingredient (valproic acid/sodium valproate) equivalent to 500 mg expressed as sodium valproate.

The blood concentration of valproate anion and in particular the maximum blood concentration ($C_{max}$), the time after administration at which this maximum concentration occurs ($T_{max}$) and the residual blood concentration 24 hours after administration were then recorded every hour, from administration, for each subject.

The results obtained are reproduced in the appended Figure III, in which figure:
a) the curve denoted "Composition A/water" represents the mean blood concentration obtained with the Composition A microspheres in water
b) the curve denoted "Composition A/yoghurt" represents the mean blood concentration obtained with the Composition A microspheres in yoghurt
c) the curve denoted "tablet" represents the mean blood concentration obtained with the divisible retard tablet.

These results show that the $C_{max}$ of the Composition A microspheres is slightly greater than that of the divisible retard tablet, i.e. approximately 16% for the microspheres in water and approximately 22% for the microspheres in yoghurt, whereas the $T_{max}$ values prove to be slightly shorter for the microspheres with respect to the tablet.

Finally, the results of the analyses of variance show that there is no significant difference between the areas under the curves (AUC).

In other words, these tests enable it to be concluded that there exists no significant difference in bioavailability between the Composition A microspheres and the divisible retard tablet.

Consequently, microspheres containing from 30% to 35% of active principle in combination with a matrix vehicle entirely composed of beeswax represent microspheres of vital importance.

Likewise, microspheres of this type, in which the active principle is formed of 25% to 35% of valproic acid and of 65% to 75% of a pharmaceutically acceptable salt of this acid, such as sodium valproate, are particularly preferred for the purposes of the invention.

Unlike other technologies for the production of spheroids, prilling makes it possible to obtain a so-called monodisperse particle size distribution with the advantage of producing spheres which are regular in size. Consequently, during the administration of the medicament containing them, the amount of such microspheres received by the patient will be constant.

The pharmaceutical microspheres of the invention possess this advantage, in that they exhibit such a regular spherical shape, with a diameter of between 250 μm and 500 μm, generally of the order of 400 μm.

If necessary, these microspheres can be covered with a film-forming agent, so as to form, for example, a gastroresistant film.

In addition, they can be packaged in various pharmaceutical forms, unitary or otherwise, suitable for oral administration. Such pharmaceutical forms can be, for example, a tablet, including a divisible tablet, a capsule, including a hard gelatin capsule, or a powder packaged, for example, in a chartula or in a system for dispensing unit doses, in particular a dispensing/measuring bottle or a container furnished with an adjustable-volume measuring spoon, for example for adjusting doses to the weight of the patient.

When they are put into pharmaceutical form, the microspheres in question can receive agents which facilitate flow, as well as lubricants, inorganic fillers, such as silicas, talc or aluminum oxide, or alternatively sweeteners, such as aspartame.

These pharmaceutical forms can advantageously comprise, per administration unit, from 50 to 500 mg of active principle in the form of microspheres according to the invention, in particular from 50 to 250 mg.

The following non-limiting Examples illustrate the invention:

Example 1

Preparation of Microspheres Containing Valproic Acid/Sodium Valproate in Beeswax Microspheres with the following composition are prepared:

|  | % by weight |
|---|---|
| White beeswax | 68.424 |
| Valproic acid | 9.576 |
| Sodium valproate | 22 |
|  | 100.00 | the preparation being carried out in the following way.

68.424 g of white beeswax are introduced into the jacketed vessel of a melting device thermostatically adjusted to 95° C. and then the wax is melted at a temperature of 90° C. to 93° C. while monitoring that the product has completely melted.

9.576 g of valproic acid and then 22.000 g of sodium valproate are then dispersed, with slow stirring, in the molten wax maintained at 90° C. and it is confirmed that the two ingredients have dissolved when the mixture becomes clear (no appearance of crystals).

The mixture is then prilled, at a temperature of 90° C., through 200 μm injectors maintained at a temperature of 87° C. to 91° C. and under a pressure of 0.5 bar. The frequency of the vibrator of the device ($5.75 \times 10^3$ to $6.70 \times 10^3$ Hz) is adjusted, so as to individualize the droplets formed, under stroboscopic monitoring at a frequency of 25,000 Hz.

Microspheres solidified by cooling during their fall in air (drop height: approximately 2.5 m) refrigerated by a countercurrent of cold air or by a liquid nitrogen bath are thus collected at the base of the device. These microspheres have a mean diameter of 400 μm.

Microspheres were prepared in the same way, but by using other matrix excipients, from the following formulations, which all proved to be clear after dissolution of the active principle (no appearance of crystals):

Example 2

|  | % by weight |
|---|---|
| Cutina ® HR | 34.185 |
| Cutina ® BW | 34.185 |
| Valproic acid | 9.63 |
| Sodium valproate | 22 |
|  | 100.00 |

Example 3

|  | % by weight |
|---|---|
| Cutina ® HR | 29.185 |
| Cutina ® BW | 29.185 |
| Monomuls ® 90-25 | 10 |
| Valproic acid | 9.63 |
| Sodium valproate | 22 |
|  | 100.00 |

Example 4

|  | % by weight |
|---|---|
| Compritol ® 888 | 58.37 |
| Labrafil ® 2130 CS | 10 |
| Valproic acid | 9.63 |
| Sodium valproate | 22 |
|  | 100.00 |

Example 5

|  | % by weight |
|---|---|
| Precirol ® ATO 5 | 58.37 |
| Labrafil ® 2130 CS | 10 |
| Valproic acid | 9.63 |
| Sodium valproate | 22 |
|  | 100.00 |

Example 6

|  | % by weight |
|---|---|
| Cutina ® HR | 24.185 |
| Cutina ® BW | 24.185 |

-continued

|  | % by weight |
|---|---|
| Monomuls ® 90-25 | 20 |
| Valproic acid | 9.63 |
| Sodium valproate | 22 |
|  | 100.00 |

Example 7

|  | % by weight |
|---|---|
| Compritol ® 888 | 68.37 |
| Valproic acid | 9.63 |
| Sodium valproate | 22 |
|  | 100.00 |

Example 8

|  | % by weight |
|---|---|
| Compritol ® 888 | 58.37 |
| Cutina ® HR | 10 |
| Valproic acid | 9.63 |
| Sodium valproate | 22 |
|  | 100.00 |

Example 9

|  | % by weight |
|---|---|
| Compritol ® 888 | 58.37 |
| Beeswax | 10 |
| Valproic acid | 9.63 |
| Sodium valproate | 22 |
|  | 100.00 |

Example 10

|  | % by weight |
|---|---|
| Compritol ® 888 | 58.37 |
| Paraffin | 10 |
| Valproic acid | 9.63 |
| Sodium valproate | 22 |
|  | 100.00 |

Example 11

|  | % by weight |
|---|---|
| Compritol ® 888 | 58.37 |
| Gelucire ® 50-02 | 10 |
| Valproic acid | 9.63 |
| Sodium valproate | 22 |
|  | 100.00 |

Example 12

|  | % by weight |
|---|---|
| Compritol ® 888 | 58.37 |
| Labrafac ® lipophile | 10 |
| Valproic acid | 9.63 |
| Sodium valproate | 22 |
|  | 100.00 |

Example 13

|  | % by weight |
|---|---|
| Compritol ® 888 | 58.37 |
| Myverol ® 18/99 | 10 |
| Valproic acid | 9.63 |
| Sodium valproate | 22 |
|  | 100.00 |

Example 14

|  | % by weight |
|---|---|
| Compritol ® 888 | 34.185 |
| Beeswax | 34.185 |
| Valproic acid | 9.63 |
| Sodium valproate | 22 |
|  | 100.00 |

Example 15

Pharmaceutical Forms Containing Microspheres

1) Chartula 756.7 mg of microspheres as prepared in Example 1 are introduced into a chartula, so as to form an oral administration unit containing 238.96 mg of active principle composed of 30.4%/69.6% by weight valproic acid/sodium valproate, which corresponds to 250 mg of active principle expressed as sodium valproate.

2) Dispenser/Measuring Bottle 24 g of microspheres prepared in Example 1, i.e. 8 g of active principle per packaged unit, are introduced into a bottle with a working volume of approximately 45 ml which allows unit doses to be dispensed. This bottle makes it possible to dispense approximately 50 unit doses containing 150 mg of active principle composed of 30.4%/69.6% by weight valproic acid/sodium valproate.

The invention claimed is:

1. Pharmaceutical microspheres, containing, as active principle, a mixture of valproic acid and of one of its pharmaceutically acceptable salts in combination with a matrix vehicle selected from the group consisting of saturated or unsaturated fatty acid glycerides, hydrogenated oils, saturated polyglyclolysed glycerides, and waxes, and their mixtures,
   the amount of active principle representing from 30% to 35% by weight of the total weight of the microspheres, thereby the dissolution of the active principle in the matrix vehicle is facilitated, wherein the active principle contains a mixture of 15% to 60% by weight of valproic acid and of 40% to 85% by weight of pharmaceutically acceptable salt of this acid,
   said microspheres being of a regular size and of a regular spherical shape having a monodisperse particle size distribution with a diameter between 250 μm and 500 μm such that the amount of said microspheres received by a patient is constant.

2. The pharmaceutical microspheres according to claim 1, wherein the pharmaceutically acceptable salt is an alkali metal salt or an alkaline earth metal salt.

3. The pharmaceutical microspheres according to claim 2, wherein the alkali metal salt is the sodium salt.

4. The pharmaceutical microspheres according to claim 2, wherein the alkaline earth metal salt is the calcium or magnesium salt.

5. The pharmaceutical microspheres according to claim 1, wherein the active principle contains a mixture of 25% to 35% by weight of valproic acid and of 65% to 75% by weight of pharmaceutically acceptable salt of this acid.

6. The pharmaceutical microspheres according to claim 1, wherein the saturated or unsaturated fatty acid glycerides contain up to 80 carbon atoms.

7. The pharmaceutical microspheres according to claim 6, wherein the saturated polyglycolysed glycerides are mixtures of glycerol monoesters, diesters, and triesters and of polyethylene glycol mono- and diesters.

8. The pharmaceutical microspheres according to claim 1, wherein the saturated or unsaturated fatty acid glycerides are glyceryl dibehenate, glyceryl palmitate/stearate, glyceryl monostearate, glyceryl monooleate, or caprylic/capric glyceride, the hydrogenated oil is hydrogenated castor oil, and the wax is natural beeswax, synthetic beeswax, or a paraffin.

9. The pharmaceutical microspheres according to claim 1, wherein the matrix vehicle is a mixture of paraffin and glyceryl dibehenate.

10. The pharmaceutical microspheres according to claim 9, wherein the pharmaceutically acceptable salt is the sodium salt.

11. The pharmaceutical microspheres according to claim 1, wherein the matrix vehicle has a melting point between 50° C. and 120° C.

12. The pharmaceutical microspheres according to claim 11, wherein the matrix vehicle has a melting point between 70° C. and 90° C.

13. The pharmaceutical microspheres according to claim 1, suitable for sustained release of the active principle such that no specific coating is required for this purpose.

14. A process for the preparation of pharmaceutical microspheres according to claim 1, wherein valproic acid and the pharmaceutically acceptable salt of this acid are added either simultaneously or sequentially to the matrix vehicle in the molten form and the resulting mixture is maintained with stirring until a clear fluid is obtained, the mixture in the clear form thus obtained is forced through a nozzle, which is subjected to vibration, whereby droplets are formed at the outlet of the nozzle and carried by gravity into a tower in which a cold gas moves in a counter-currentwise direction, and the microspheres are collected in the bottom of the tower.

15. A pharmaceutical powder for oral administration comprising microspheres according to claim 1, the powder optionally containing agents that facilitate flow, lubricants, inorganic fillers and/or sweeteners.

16. The pharmaceutical powder according to claim 15, wherein the inorganic filler is a silica, talc, or aluminum oxide and the sweetener is aspartame.

17. The pharmaceutical powder according to claim 15, packaged in chartulas.

18. The pharmaceutical powder according to claim 15, packaged in systems for dispensing unit doses.

19. Pharmaceutical microspheres comprising, in combination,
   a) as active principle a mixture of (i) valproic acid and (ii) one of its pharmaceutically acceptable salts, and
   b) a matrix vehicle selected from the group consisting of glycerol ester, hydrogenated oil, esterified polyethylene glycol, wax, and a mixture thereof,
   wherein the microspheres have a monodisperse particle size distribution with a diameter between 250 μm and 500 μm,
   wherein the amount of active principle is about 35% by weight of the total weight of the pharmaceutical microspheres, and
   wherein the pharmaceutical microspheres do not have sustained-release coating and have a regular size and a regular spherical shape and are suitable for (i) an immediate release formulation of the active principle or (ii) a sustained release formulation of the active principle.

20. The pharmaceutical microspheres of claim 19 having a sustained-release profile.

21. The pharmaceutical microspheres of claim 1 prepared by a process comprising:
   adding, simultaneously or sequentially, the pharmaceutically acceptable salt of the acid to the matrix vehicle in molten form;
   maintaining the resulting mixture, with stirring, until a clear fluid is obtained;
   forcing the resulting mixture in clear form through a nozzle, which is subjected to vibration to form droplets at the outlet of the nozzle;
   conveying the droplets by gravity into a tower in which a cold gas moves in a countercurrent direction to movement of the droplets; and
   collecting the microspheres from the tower.

22. The pharmaceutical microspheres of claim 1, wherein the matrix vehicle comprises glycerol dibehenate.

23. Pharmaceutical microspheres, containing, as active principle, a mixture of valproic acid and of one of its pharmaceutically acceptable salts in combination with a matrix vehicle selected from the group consisting of saturated or unsaturated fatty acid glycerides, hydrogenated oils, saturated polyglyclolysed glycerides, and waxes, and their mixtures,
   the amount of active principle comprising from 30% to 35% by weight of the total weight of the microspheres, thereby the dissolution of the active principle in the matrix vehicle is facilitated, wherein the active principle contains a mixture of 25% to 35% by weight of valproic acid and of 65% to 75% by weight of pharmaceutically acceptable salt of this acid, said microspheres being prills of a regular size and of a regular spherical shape having a monodisperse particle size distribution with a diameter between 250 μm and 500 μm such that the amount of said microspheres received by a patient is constant.

24. The pharmaceutical microspheres according to claim 23, wherein the salt is the sodium salt of valproic acid.

25. The pharmaceutical microspheres according to claim 24, wherein the matrix vehicle is a mixture of paraffin and glyceryl dibehenate.

26. The pharmaceutical microspheres according to claim 25, suitable for sustained release of the active principle such that no specific coating is required for this purpose.

27. Pharmaceutical microspheres, containing, as active principle, a mixture of valproic acid and of one of its pharmaceutically acceptable salts in combination with a matrix vehicle, the amount of active principle consisting of from 30% to 35% by weight of the total weight of the microspheres, thereby the dissolution of the active principle in the matrix vehicle is facilitated, wherein the active principle contains a mixture of 15% to 60% by weight of valproic acid and of 40% to 85% by weight of pharmaceutically acceptable salt of this acid, said microspheres being prills of a regular size and of a regular spherical shape having a monodisperse particle size distribution with a diameter between 250 μm and 500 μm such that the amount of said microspheres received by a patient is constant, wherein the matrix vehicle selected is from glycerol esters, hydrogenated oils, esterified polyethylene glycols, or waxes, and their mixtures, having a melting point between 70° and 90° C., and wherein the matrix vehicle does not contain added surface active agents.

28. The pharmaceutical microspheres according to claim 1, containing at most 35% by weight of active principle.

* * * * *